US00PP23151P2

(12) United States Plant Patent
Brown

(10) Patent No.: US PP23,151 P2
(45) Date of Patent: Oct. 30, 2012

(54) ***LEUCANTHEMUM* PLANT NAMED 'LWMWH03-0'**

(50) Latin Name: ***Leucanthemum* hybrid**
Varietal Denomination: LWMWH03-0

(75) Inventor: Graham Brown, Pennant Hills (AU)

(73) Assignee: NuFlora International

( * ) Notice: Subject to any disclaimer, the term of this patent is extended or adjusted under 35 U.S.C. 154(b) by 0 days.

(21) Appl. No.: 13/068,511

(22) Filed: May 13, 2011

(51) Int. Cl.
*A01H 5/00* (2006.01)

(52) U.S. Cl. ..... Plt./285

(58) Field of Classification Search ..... Plt./285
See application file for complete search history.

*Primary Examiner* — Annette Para

(74) *Attorney, Agent, or Firm* — Cassandra Bright

(57) ABSTRACT

A new and distinct *Leucanthemum* hybrid cultivar named 'LWMWH03-0' is disclosed, characterized by large white daisy type flowers, and early flowering. Plants of the new variety flowering flower repeatedly. The new variety is an *Leucanthemum* hybrid, and naturally blooms from Spring to early Fall.

1 Drawing Sheet

Latin name of the genus and species: *Leucanthemum* hybrid.

Variety denomination: 'LWMWH03-0'.

BACKGROUND OF THE INVENTION

The new variety was discovered, by the inventor, Graham Brown, a citizen of Australia as the result of a planned breeding program. The inventor crossed the seed parent, an unpatented proprietary *Leucanthemum* hybrid seedling referred to as '05.1.1' and the pollen parent, an unpatented, proprietary *Leucanthemum* hybrid seedling referred to as '05.1.2'. The crossing resulting in 'LWMWH03-0' was made in November of 2006. It was discovered by Graham Brown in November 2007 a research greenhouse in Cobbitty, New South Wales, Australia.

Asexual reproduction of the new cultivar 'LWMWH03-0' by vegetative cuttings was performed in Cobbitty, Australia in December 2007 and has shown that the unique features of this cultivar are stable and reproduced true to type in successive generations. Approximately 10 generations have been reproduced.

SUMMARY OF THE INVENTION

The cultivar 'LWMWH03-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LWMWH03-0' These characteristics in combination distinguish 'LWMWH03-0' as a new and distinct *Leucanthemum* cultivar:

1. Early flowering
2. Continuous repeat flowering.
3. Large flowers.

PARENT COMPARISON

Plants of the new cultivar 'LWMWH03-0' are similar to plants of the seed parent variety, in most horticultural characteristics, however, plants of 'LWMWH03-0' flower earlier and produce larger flowers than the seed parent.

Plants of the new cultivar 'LWMWH03-0' are similar to plants of the pollen parent variety, in most horticultural characteristics, however, plants of 'LWMWH03-0' flower earlier and produce larger flowers than the pollen parent.

PARENT COMPARISON

Plants of the new cultivar 'LWMWH03-0' are similar to plants of the commercial variety *Leucanthemum* 'Angel,' U.S. Plant Pat. No. 14,289 in most horticultural characteristics. However, plants of the new cultivar 'LWMWH03-0' differ in the following characteristics;

1. 'LWMWH03-0' has a single daisy flower form, whereas 'Angel' has a somewhat anemone type flower.
2. 'LWMWH03-0' has a larger width inflorescence.
3. 'LWMWH03-0' flowers one week later on average than 'Angel'.
4. Plants of 'LWMWH03-0' are taller than plants of 'Angel'.

Plants of the new cultivar 'LWMWH03-0' are also similar to plants of the unpatented commercial variety *Leucanthemum* 'Becky' US Plant Patent Number in most horticultural characteristics. However, plants of the new cultivar 'LWMWH03-0' differ in the following characteristics;

1. 'LWMWH03-0' flowers earlier than 'Becky'.
2. Plants of 'LWMWH03-0' repeat flowering, whereas 'Becky' does not continuously flower.
3. Plants of 'LWMWH03-0' are shorter than plants of 'Becky'.
4. Plants of 'LWMWH03-0' produce more flowers than plants of 'Becky'.

BRIEF DESCRIPTION OF THE PHOTOGRAPH

The accompanying photograph in FIG. 1 illustrates in full color a typical plant of 'LWMWH03-0' grown in a greenhouse. The pot size is a commercial 1 gallon container, approximately 17 cm tall and 15 cm in diameter. The plant shown is approximately 20 weeks old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'LWMWH03-0' plants grown in a greenhouse in Lompoc, Calif. from Fall 2007 to Spring 2008. The growing temperature ranged from 15° C. to 16° C. at night to 15° C. to 32° C. during the day. Measurements and numerical values represent averages of typical flowering types.

Botanical classification: *Leucanthemum* hybrid 'LWMWH03-0'.

PROPAGATION

Time to rooting: Approximately 20 days at approximately 20° C.

Root description: Fine, fibrous.

PLANT

Growth habit: Upright perennial.
Height: Approximately 30 cm.
Blooming period: Naturally blooming Spring to early Fall.
Plant spread: Approximately 45 cm.
Growth rate: Moderate to vigorous.
Branching characteristics: Moderately free branching.
Length of lateral branches: Approximately 10 cm.
Diameter of lateral branches: Approximately 0.6 cm.
Quantity of lateral branches: Approximately 5.
Texture of lateral branches: Lightly pubescent, ridged due to hextangular stem.
Color of lateral branches: Near RHS Green 137C.
Aspect: Upright.
Number of leaves per lateral branch: Approximately 12.
Age of plant described: Approximately 20 weeks from an unrooted cutting.

FOLIAGE

Leaf:
- *Arrangement*.—Alternate, simple.
- *Average length*.—Approximately 8.1 cm.
- *Average width*.—Approximately 1.6 cm.
- *Shape of blade*.—Oblanceolate.
- *Apex*.—Acute.
- *Base*.—Attenuate.
- *Attachment*.—Sessile.
- *Margin*.—Dentate.
- *Texture of top surface*.—Smooth.
- *Texture of bottom surface*.—Smooth.
- *Leaf internode length*.—Approximately 3.0 cm.
- *Color*.—Young foliage upper side: Near Green 137A. Young foliage under side: Near Green 137C. Mature foliage upper side: Near Green 137A. Mature foliage under side: Near Green 137C.
- *Venation*.—Type: Pinnate. Venation color upper side: Near Green 137A. Venation color under side: Near Green 137C.

FLOWER

Bloom period: Naturally blooming from Spring to early Fall.

Bud:
- *Bud shape*.—Flattened sphere.
- *Bud length*.—Approximately 1.4 cm.
- *Bud diameter*.—Approximately 0.9 cm.
- *Bud color*.—Near Green 137A.

Inflorescence:
- *Form*.—Single composite type daisy. Occurring mainly on upright terminal peduncles. Infrequently occurring on lateral peduncles.

Flower:
- *Diameter of entire flower*.—Approximately 6.5 cm.
- *Depth of flower*.—Approximately 1.6 cm.
- *Width of disc*.—Approximately 1.7 cm.
- *Depth of disc*.—Approximately 1.3 cm.

Ray florets:
- *Number of ray florets*.—Avg. 45.
- *Length*.—Approximately 2.1 cm.
- *Width*.—Approximately 0.6 cm.
- *Apex shape*.—3 obtuse lobes.
- *Margin*.—Entire.
- *Texture*.—Smooth.
- *Aspect*.—Flat.

Color:
- *Ray florets*.—Upper surface at first opening: Near White 155A. Upper surface at maturity: Near White 155D. Upper surface at fading: Near White 155A. Under surface at first opening: Near White 155A. Under surface at maturity: Near White 155C. Under surface at fading: Near White 155A.
- *Disc florets*.—Number of Disc Florets: More than 200. Length: Approximately 0.5 cm. Width: Approximately 0.08 cm. Shape: Cylindric. Margin: Entire. At first opening: Near Yellow-Orange 1yB. At maturity: Near Yellow-Orange 14A. At fading: Near Yellow-Orange 22A.

Fragrance: Slightly musty.

Involucral bracts/phyllaries:
- *Number*.—Approximately 45.
- *Length*.—Approximately 0.5 cm.
- *Width*.—Approximately 0.3 cm.
- *Apex*.—Acute.
- *Margin*.—Entire.
- *Color*.—Inside sepal color near R.H.S. Green 137C and outside sepal color near R.H.S. Green 137B.

REPRODUCTIVE ORGANS

Androecium: Present on disc florets only.
- *Stamens*.—4.
- *Anther length*.—Approximately 0.03 cm.
- *Anther color*.—Near Yellow-Orange 14B.
- *Pollen color*.—Near Yellow-Orange 15A.

Gynoecium: Present on ray and disc florets.

Ray florets:
- *Number of pistils per flower*.—1. Stigma shape: Two parted. Stigma color: Near Yellow 12A. Style color: Near Yellow 4B. Style length: Approximately 0.2 cm.

Disc florets:

*Number of pistils per flower.*—1. Stigma shape: Cylindric. Stigma color: Near Yellow 12A. Style color: Near Yellow 2C. Style length: Approximately 0.1 cm.

OTHER CHARACTERISTICS

Disease resistance: Neither resistance nor susceptibility to diseases or pests has been observed in this variety to date.

Temperature tolerance: Hardy perennial. Hardy to at least −2° C., high temperature tolerance to at least 35° C.

Fruit/seed production: Fruit and seed production have not been observed in the new cultivar.

What is claimed is:

1. A new and distinct cultivar of *Leucanthemum* plant named 'LWMWH03-0' as herein illustrated and described.

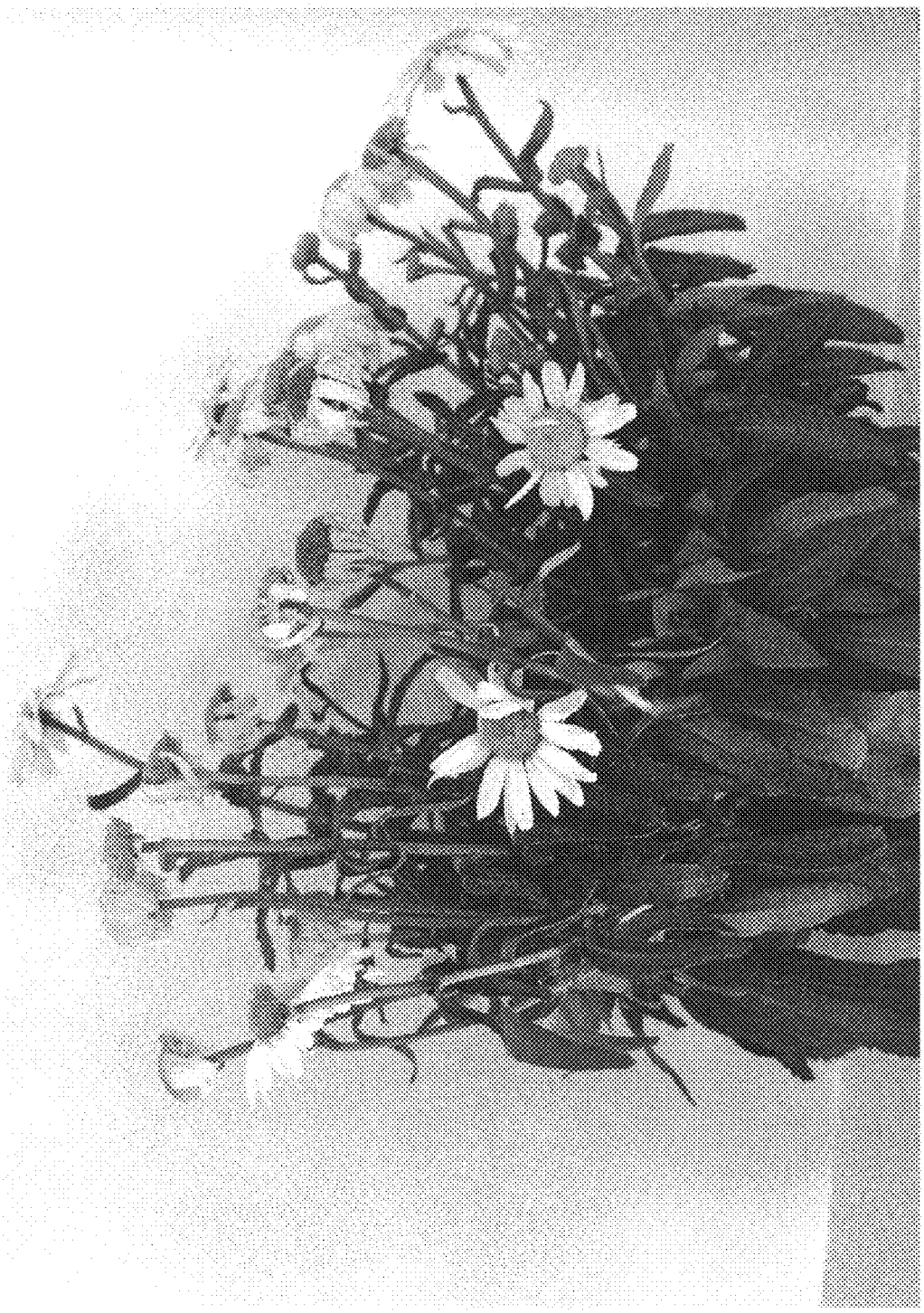

* * * * *